(12) United States Patent
Lutz et al.

(10) Patent No.: US 6,946,427 B2
(45) Date of Patent: Sep. 20, 2005

(54) PRESERVATIVE BLENDS CONTAINING IODINE CONTAINING COMPOUNDS

(75) Inventors: Patrick Jay Lutz, Nazareth, PA (US); Olga Borokhov, Chatham, NJ (US); Susan Alcorn Ban, Kunkletown, PA (US)

(73) Assignee: Lonza Inc., Fair Lawn, NJ (US)

( * ) Notice: Subject to any disclaimer, the term of this patent is extended or adjusted under 35 U.S.C. 154(b) by 453 days.

(21) Appl. No.: 10/087,206

(22) Filed: Feb. 28, 2002

(65) Prior Publication Data

US 2004/0143011 A1 Jul. 22, 2004

Related U.S. Application Data

(60) Provisional application No. 60/273,079, filed on Mar. 1, 2001.

(51) Int. Cl.$^7$ .................. A01N 37/40; A01N 43/16; A01N 47/12
(52) U.S. Cl. .................. 504/140; 504/143; 504/300; 504/324; 514/460; 514/479
(58) Field of Search .................. 504/140, 143, 504/300, 324, 149; 514/460, 479, 563, 455, 456, 457

(56) References Cited

U.S. PATENT DOCUMENTS 3,097,131 A   7/1963   Ueno et al. .................. 167/31
4,844,891 A   7/1989   Rosen et al. .................. 424/76
5,073,570 A   12/1991  Tseng .................. 514/533
5,670,160 A   9/1997   Eggensperger et al. ..... 424/405
5,885,593 A   3/1999   Epstein .................. 424/401
5,906,981 A   5/1999   Gaglani
2001/0031668 A1 * 10/2001 Gueret .................. 401/124

FOREIGN PATENT DOCUMENTS

| EP | 0 228 943 | * | 7/1987 | |
| JP | 5350245 | | 5/1978 | C08K/5/09 |
| JP | 57057624 | | 4/1982 | A61K/31/19 |
| JP | 57058625 | | 4/1982 | A61K/31/19 |
| JP | 4049207 | | 2/1992 | A01N/25/04 |
| JP | 6-313269 | | 11/1994 | D06M/13/425 |
| JP | 6313269 | | 5/1999 | A01N/47/10 |

OTHER PUBLICATIONS

International Search Report.

* cited by examiner

Primary Examiner—S. Mark Clardy
(74) Attorney, Agent, or Firm—Darby & Darby

(57) ABSTRACT

Applicants have discovered that cyclic and acyclic ketone acids, such as dehydroacetic acid, and salts thereof as well as an aromatic carboxylic acid and salts thereof enhance the performance of iodine containing biocides as antimicrobial agents and preservatives. The present invention provides a composition comprising (a) an iodine containing biocide; and (b) (i) a ketone acid or salt thereof, (ii) an aromatic carboxylic acid or a salt thereof, or (iii) a mixture thereof. Preferably, the ketone acid is a cyclic ketone acid and the aromatic carboxylic acid is salicylic acid.

29 Claims, No Drawings

PRESERVATIVE BLENDS CONTAINING IODINE CONTAINING COMPOUNDS

This application claims the benefit of U.S. Provisional Application Ser. No. 60/273,079, filed Mar. 1, 2001, which is hereby incorporated by reference.

FIELD OF THE INVENTION

This invention relates to antimicrobial compositions containing (a) an iodine containing biocide, such as 3-iodo-2-propynyl butyl carbamate, and (b) (i) a cyclic or acyclic ketone acid or a salt thereof, (ii) an aromatic carboxylic acid or a salt thereof, or (iii) a mixture thereof.

BACKGROUND OF THE INVENTION

Many iodine containing compounds, such as 3-iodo-2-propynyl butyl carbamate (IPBC), are known to be effective as antimicrobial agents and preservatives. However, IPBC and many other iodine containing compounds are expensive. As a result, there is a continuing need for improved antimicrobial and preservative compositions which contain low concentrations of iodine containing biocides.

SUMMARY OF THE INVENTION

Applicants have discovered that ketone acids, aromatic carboxylic acids, and salts thereof synergistically enhance the performance of iodine containing biocides. The present invention provides a composition comprising
(a) an iodine containing biocide; and
(b) (i) a ketone acid or salt thereof,
  (ii) an aromatic carboxylic acid or a salt thereof, or
  (iii) a mixture thereof.
Preferably, the ketone acid is a cyclic ketone acid. The aforementioned mixtures are synergistic.

Another embodiment of the present invention is a method for inhibiting the growth of microorganisms on a substrate by applying an antimicrobial or preserving effective amount of the composition of the present invention.

DETAILED DESCRIPTION OF THE INVENTION

The term "biocide", but is not limited to, bactericides, fungicides, pesticides and agents which inhibit the growth of and/or destroy microorganisms and insects.

The present invention provides a composition comprising (a) an iodine containing compound; and (b) (i) a ketone acid or salt thereof, (ii) an aromatic carboxylic acid or a salt thereof, or (iii) a mixture thereof. Preferably, the ketone acid is a cyclic ketone acid. The ketone acid and aromatic carboxylic acid enhances the biocidal efficacy of the iodine containing biocide. These compositions are useful as antimicrobial, fungicidal, and actericidal agents and as preservatives in the papermaking, textile, agricultural, and coating industries and personal care, household, industrial, and institutional products, such as starches, paints, adhesives, polyvinyl chloride and other plastics, and melt-working fluids. The preservative system may be incorporated into substrates susceptible to microbial growth. For example, the preservative system may be incorporated into or be a personal care product, such as a shampoo, conditioner, cream, lotion, cosmetic, and soap; a household product, such a fabric softener, laundry detergent, and hard surface cleaner; or an industrial product, such as paint, wood, textile, adhesive, sealant, leather, rope, paper pulp, plastic, fuel, oil, rubber working fluid, and metal working fluid.

Examples of compounds which may be used as the iodine containing biocide component of the invention are fungicidally active iodoalkynyl derivatives. These include compounds derived from propyne or iodopropynyl alcohols, such as the esters, ethers, acetals, carbamates and carbonates and the iodopropynyl derivatives of pyrimidines, triazolinones, tetrazoles, triazinones, sulfamides, benzothiazoles, ammonium salts, carboxamides, hydroxamates, and ureas.

Iodine Containing Compounds

Preferred iodine containing biocides include, but not limited to, 3-iodo-2 propynyl derivatives such as 3-iodo-2-propynyl butyl carbamate, 3-iodo-2-propynyl succinate and p-chlorophenyl-3-iodopropynyl formal; iodo sulfone derivatives; and triiodoallyl alcohols.

Preferably, iodopropynyl carbamate compounds have the formula:

$$\left[ I-C\equiv C-(CHR)_z-\overset{O}{\underset{\|}{C}}-NH \right]_q -R \qquad I$$

wherein R is selected from the group consisting of hydrogen, and substituted and unsubstituted alkyl, aryl, and alkylaryl groups having from 1 to 20 carbon atoms; and q and z independently are integers from 1 to 3.

Suitable iodopropynyl ester compounds include, but are not limited to, those having the formulae:

$$I-C\equiv C-(CHR)_y-O-\overset{O}{\underset{\|}{C}}-\overset{R^4}{\underset{|}{C}}-R^2$$

$$X^+-O-\overset{O}{\underset{\|}{C}}-\overset{W}{\underset{|}{C}}-R^1 \quad \text{and} \qquad II$$
$$\phantom{X^+-O-\overset{O}{\underset{\|}{C}}-}\underset{R^3}{|}$$

$$I-C\equiv C-(CHR)_y-O-\overset{O}{\underset{\|}{C}}-C-R^2 \qquad III$$
$$X^--O-\overset{}{\underset{\|}{C}}-\overset{\|}{\underset{O}{C}}-R^1$$

wherein:

$R_1$ and $R^2$ are defined as $R^3$ and $R^4$ below or are joined to form a cycloalkyl, cycloalkenyl, aromatic or a heterocyclic ring containing an oxygen, nitrogen or sulfur atom or an alkoxy, amino, carboxyl, halo, hydroxyl, keto or a thiocarboxyl-substituted derivative thereof;

$R_3$ and $R_4$ are independently selected from
(A) hydrogen, alkyl, cycloalkyl, alkenyl, cycloalkenyl, aryl, a heterocyclic ring containing an oxygen, nitrogen or sulfur atom, alkoxy, amino, carboxyl, halo, hydroxyl, keto or a thiocarboxyl; and
(B) substituted derivatives of the alkyl, cycloalkyl, alkenyl, cycloalkenyl, aryl and the heterocyclic ring wherein the substitutions are alkyl, cycloalkyl, alkenyl, cycloalkenyl, aryl, alkoxy, amino, carboxyl, halo, hydroxyl, keto or a thiocarboxyl;

y is an integer from 0 to 16;

W is a single bond, oxygen, $-N(R^5)-$ or $-(CR^6R^7)_p-$;

$R^5$ is hydrogen, alkyl, cycloalkyl, alkenyl, cycloalkenyl, aryl or a heterocyclic ring containing an oxygen, nitrogen or sulfur atom or a substituted derivative of alkyl, cycloalkyl, alkenyl, cycloalkenyl or aryl groups wherein the substitutions are alkyl, cycloalkyl, alkenyl, cycloalkenyl, aryl, alkoxy, amino, carboxyl, halo, hydroxyl, keto, or a thiocarboxyl;

$R^6$ and $R^7$ are defined as $R^3$ and $R^4$ above;

p is an integer from 1 to 12; and

X is hydrogen or a salt-forming cation such as an alkali metal, an alkaline earth metal, ammonium, tertiary ammonium, a quaternary ammonium, a biguanide or a polybiguanide.

The above definition of $R_5$ includes, among other things, an aminoalkyl group.

The heterocyclic rings referred to in the above definitions may contain from 5 to 8 members, the alkyl or cycloalkyl groups from 1 to 18 atoms, the alkenyl or cycloalkenyl groups from 2 to 18 carbon atoms, and the aryl groups from 6 to 10 members.

In formula III, when $R_1$ and $R^2$ are hydrogen, the compound is a maleate. When $R_1$ and $R^2$ are joined together to form part of a six membered aromatic ring the compound is a phthalate. In formula II, when $R_1$, $R^2$, $R^3$, and $R^4$ are hydrogen and W is a single bond, the compound is a succinate. When $R_1$, $R^2$, $R^3$ and $R^4$ are hydrogen and W is an oxygen, the compound is a diglycolate. Other compounds include the mono-iodopropynyl esters of anhydrides such as ethylenediamine tetraacetic dianhydride, 3,3-dimethylglutaric anhydride, S-acetylmercaptosuccinic anhydride, dichloromaleic anhydride, 2-dodecen-1-yl succinic anhydride and cis-5-norbomene-endo-2,3-dicarboxylic anhydride. Where hydrophilicity is desired, the sodium salts may be used because of their extremely high water solubility. Preferred carboxylic acid anhydrides include, but are not limited to, succinic, itaconic, phthalic, tetrachlorophthalic and diglycolic anhydride. Examples of such compounds are described in U.S. Pat. Nos. 4,844,891 and 5,073,570.

More preferably, the iodine containing biocide is 3-iodo-2-propynyl butyl carbamate (IPBC). The IPBC may be any grade of IPBC including, but not limited to, an essentially pure commercial grade IPBC in solid form and commercially available 6% and 10% grades in a solvent.

Another class of suitable iodopropynyl compounds are those having the formula:

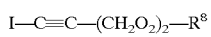

where $R^8$ is benzyl or benzyl substituted with a methyl, methoxy, carboxyl, halogen or nitro group. A preferred compound is p-chlorophenyl-3-iodopropynyl formal.

The iodine containing biocide may optionally be encapsulated, such as, for example, in cyclodextrin; calixarenes, such as 4-tert-butylcali[4]arene; liposomes; catezones; and amphiphilic betaine polymers. One example of an encapsulated iodine containing biocide is IPBC encapsulated in cyclodextrin, available as Troy Polyphase 604 from Troy Chemical Co. of East Hanover, N.J.

Ketone Acids

The ketone acid may be a cyclic or acyclic ketone acid. The term "cyclic ketone acid" as used herein includes compounds that have a ring containing a carbonyl group.

Suitable cyclic ketone acids include, but are not limited to, those having the formula

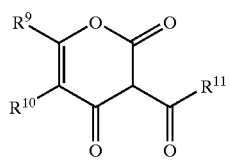

and salts thereof, wherein $R^9$, $R^{10}$, and $R^{11}$ are independently $C_1$–$C_{10}$ alkyl, $C_1$–$C_{10}$ alkenyl, $C_1$–$C_{10}$ aldenyl, aryl, aryl substituted with halogen, or ($C_1$–$C_{10}$ alkyl)aryl. Preferably, $R^9$, $R^{10}$, and $R^{11}$ are independently $C_1$–$C_4$ alkyl; or $R^9$ and $R^{10}$ form a 5–12 member ring. Preferred cyclic ketone acids, include, but are not limited to, those having the formula

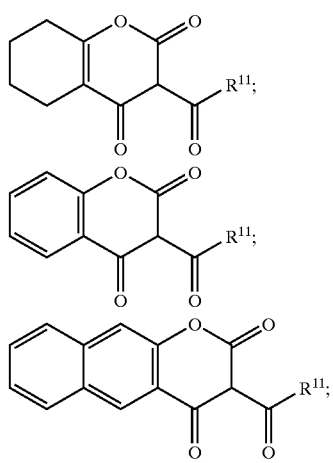

and salts thereof. A more preferred cyclic ketone acid is dehydroacetic acid and salts thereof (including hydrated thereof, such as sodium dehydroacetate (e.g. sodium dehydroacetate hydrate and sodium dehydroacetate monohydrate).

The cyclic ketone acid may optionally be encapsulated by any method in the art to increase its solubility in a desired solvent or formulation. For example, the cyclic ketone acid may be encapsulated in cyclodextrin; calixarenes, such as 4-tert-butylcali[4]arene; liposomes; catezones; and amphiphilic betaine polymers.

A preferred combination of cyclic ketone acid and ioidine containing biocide is dehydroacetic acid and IPBC.

Aromatic Carboxylic Acids

Suitable aromatic carboxylic acids include, but are not limited to, benzoic acids, derivatives thereof, and salts thereof. According to one embodiment, the aromatic carboxylic acid has the formula

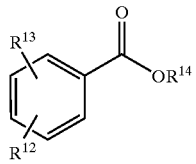

where $R^{12}$ and $R^{13}$ are independently H, —OH, or —OC(O)CH_3$; and $R^{14}$ is H, Na, K, Ca, or Mg. When $R^{14}$ is Ca or Mg, the ratio or aromatic carboxylic acid to Ca or Mg may be 1:1 or 2:1.

For example, the aromatic carboxylic acid can be a hydroxy benzoic acid, derivative thereof, or salt thereof. A preferred hydroxy benzoic acid is salicylic acid and salts thereof. Suitable salts of salicylic acid include, but are not limited to, sodium salicylate.

A preferred combination of salicylic acid or salt thereof and iodine containing biocide is sodium salicylate and IPBC.

The composition may include a solvent, such as water and water miscible solvents, including, but not limited to, alcohols, glycols (e.g. glycerin, diglycerin, butylene glycol, butoxydiglycol, propylene glycol, and dipropylene glycol), esters, ethers, polyethers, and any combination of any of the foregoing. For example, the solvent may comprise water and an alcohol, such as phenoxyethanol and/or benzyl alcohol.

Other adjuvants may be included in the composition as known to one of ordinary skill in the art. Suitable adjuvants include, but are not limited to, preservatives; solubilizing agents; chelating agents, such as ethylenediaminetetraacetic acid (EDTA) and salts thereof and zeolites; surfactants, such as cationic, anionic, nonionic, and amphoteric surfactants; antioxidants, such as butylated hydroxyanisole (BHA) and butylhydroxytoluene (BHT); amine oxides; tertiary amines; hydrotropes; zinc compounds; hydrotropes; flouride compounds; magnesium salts; calcium salts; carboxylic acids; phosphates; phosphonates; formaldehyde donors; glycereth-7; myristyl myristate; glutaraldehydes; biguanides; natural products, such as usnic acid and tea tree oils; and any combination of any of the foregoing.

Suitable preservatives include, but are not limited to, quaternary ammonium chlorides, such as benzethonium chloride (available as Hyamine® 1622 from Lonza Inc. of Fair Lawn, N.J.) and benzalkonium chlorides (available as Barquat® MB-50 and MB-80 from Lonza Inc. of Fair Lawn, N.J.); hydantoins, such as dimethylhydantoin and halogenated hydantoins; isothiazolinones; parabens, such as methylparaben, ethylparaben, and propylparaben; chloroxylenol; chlorhexidine; phenoxyethanol; benzyl alcohol; phenethyl alcohol; benzoic acid and salts thereof; chlorobutanol; sorbic acid and salts thereof; triclosan; triclocarban; and any combination of any of the foregoing.

Typically, the composition is an aqueous or oil based system and is not an emulsion. For compositions which are oil based, the iodine containing biocide is preferably not encapsulated and the ketone acid is preferably not a hydrate. A suitable solvent for an oil based system is phenoxyethanol. For compositions which are water based, the iodine containing biocide is preferably encapsulated to enhance its water solubility and the ketone acid is preferably a hydrate.

The composition can be a liquid or a solid.

The weight ratio of (1) ketone acid, aromatic carboxylic acid, or salts thereof or mixtures thereof to (2) iodine containing biocide broadly ranges from about 0.0006:1 to about 1990:1 and preferably ranges from about 0.0063:1 to about 1400:1. According to another embodiment, the molar ratio ranges from 0.063:1 to about 140:1 or from about 0.63:1 to about 14:1.

To prepare a formulation containing the composition of the present invention, a concentrate is generally first prepared. Table A illustrates the components and the ranges of components present in a typical concentrate (based upon 100% total weight of concentrate).

TABLE A

| Ranges | Iodine Containing Biocide | Ketone Acid, Aromatic Carboxylic Acid, Salts Thereof, or Mixtures Thereof |
| --- | --- | --- |
| Broad | from about 0.05 to about 80% | from about 0.05 to about 99.5% |
| Preferred | from about 0.5 to about 30% | from about 0.50 to about 70% |
| More Preferred | from about 1 to about 15% | from about 5 to about 40% |

Before use, the concentrate is diluted, preferably with the same solvent as was used in the concentrate. Use dilutions of the composition typically comprise a biocidally, fungicidally, or bactericidally effective amount of (1) the iodine containing biocide (i.e., component (a)) and/or (2) the mixture of components (a) and (b) (where component (b) is the ketone acid, aromatic carboxylic acid, or salt thereof, or a mixture thereof). The use dilutions also typically comprise a biocidal, fungicidal, or bactericidal enhancing (or potentiating) effective amount of the ketone acid or salt thereof, aromatic carboxylic acid or salt thereof, or mixture thereof (i.e., component (b)). Generally, use dilutions contain from about 0.0001%, 0.01%, or 0.1% to about 2% by weight of the concentrate. According to one preferred embodiment, use dilutions contain from about 0.1 to about 0.5% or 1% by weight of the concentrate.

Table B illustrates the components and generally the ranges of components present in the use dilution (based upon 100% total weight of use dilution).

TABLE B

| Ranges | Iodine Containing Biocide | Ketone Acid, Aromatic Carboxylic Acid, Salts Thereof, or Mixtures Thereof |
| --- | --- | --- |
| Broad | from about 0.00005 to about 0.40% | from about 0.00005 to about 0.4975% |
| Preferred | from about 0.0005 to about 0.15% | from about 0.0005 to about 0.35% |
| More Preferred | from about 0.001 to about 0.075% | from about 0.005 to about 0.2% |

Another embodiment of the present invention is a method for inhibiting the growth of microorganisms, bacteria (e.g., *S. aureus* (ATCC # 6538), *P. aeruginosa* (ATCC # 9027), and *E. coli* (ATCC # 8739)), and/or fungi (e.g., *Candida albicans* and *Aspergillus niger*) on a substrate by applying an antimicrobial, bactericidal, or fungicidal effective amount of the composition of the present invention to the substrate. The composition may be applied to the substrate by any method known to one of ordinary skill in the art including, but not limited to, brushing, dipping, soaking, vacuum impregnation, and pressure treatment.

The composition of the present invention may be prepared by mixing the ketone acid or salt thereof and/or the aromatic carboxylic acid or salt thereof, the iodine containing biocide, solvents, and adjuvants. The mixture may be heated and/or stirred to expedite mixing.

Description of the Preferred Embodiments

The following examples illustrate the invention without limitation. All parts and percentages are given by weight unless otherwise indicated.

EXAMPLE 1

Each anionic shampoo sample in Table 1 below was tested as follows. A standardized mixed bacterial solution was prepared according to the following procedure. 3 agar stabs of S. Aureus (ATCC # 6538), P. aeruginosa (ATCC # 9027), and E. Coli (ATCC # 8739) were separately incubated at about 35° C. for about 24 hours. Each stab was then washed with 3 mL of sterile 0.85% saline solution. The washes of the 3 stabs were pooled together to form an organism mixture. The absorbance of the organism mixture at 530 nm was adjusted to about 1.00 by adding saline. The spectrometer was calibrated with a saline blank. A 5 mL aliquot of the organism mixture was mixed together to produce the standardized mixed bacterial solution. Then, 40 g of each shampoo sample was inoculated with 0.2 mL of the standardized mixed bacterial solution and mixed. 1 g of the mixture was added to a sterile 20×150 mm screw cap test tube.

9 mL of sterile D/E neutralizer broth was added to the test tube and mixed to form a $10^{-1}$ dilution. Serial dilutions were prepared through to a $10^{-6}$ dilution with phosphate buffered water. The serial dilutions were plated onto Tryptic Soy Agar and incubated for 2 days at about 35° C. Bacteria counts were performed after 0 and 14 days. The results are shown in Table 1.

The anionic protein shampoo composition was comprised of 35% by weight of sodium lauryl ether sulfate; 25% by weight of triethanolamine lauryl sulfate; 3% by weight coconut diethanolamide (cocamide DEA); 1% by weight of hydrolyzed collagen, available as Polypro 5000™ from Hormel Foods of Austin, Minn.; and 36% by weight of deionized water.

The sodium dehydroacetate monohydrate, sodium salicylate, and IPBC (Glycacil® 2000) shampoo samples were prepared by mixing the appropriate amounts of the preservatives and the aforementioned protein shampoo composition and heating the mixture to about 50° C. for about 15 minutes.

TABLE 1

| Shampoo | S. aureus, P. aeruginosa, and E. coli (cfu/g) | |
|---|---|---|
| | Day 0 | Day 14 |
| Unpreserved Protein Shampoo Composition | 3.0 × 10⁶ | 3.0 × 10⁷ |
| 0.5% Sodium Salicylate¹ and 0.5% Glycacil® 2000²* | 3.0 × 10⁶ | <10 |
| 0.10% Sodium Dehydroacetate Monohydrate³, 0.10% Sodium Salicylat¹, and 0.50% Glycacil® 2000²* | 3.0 × 10⁶ | <10 |
| 0.25% Sodium Dehydroacetate Monohydrate³, 0.25% Sodium Salicylate¹, and 0.25% Glycacil® 2000²* | 3.0 × 10⁶ | <10 |
| >0.5% Sodium Dehydroacetate Monohydrate³* | 3.0 × 10⁶ | 4.0 × 10³ |
| >1.0% Sodium Salicylate¹* | 3.0 × 10⁶ | 5.0 × 10² |
| >1.0% Glycacil® 2000²* | 3.0 × 10⁶ | 1.0 × 10⁷ |

All percentages in Table 1 are in percent by weight based upon 100% by weight of total shampoo.
¹Sodium dehydroacetate monohydrate is available from Lonza Inc. of Fair Lawn, NJ.
²Glycacil ® 2000 is iodopropynyl butylcarbamate and is available from Lonza Inc. of Fair Lawn, NJ.
³Sodium salicylate is available from Sigma Chemical Co. of St. Louis, MO.
*Below the specified concentration of preservative, the shampoo contained ≧10 cfu/g after 14 days.

Synergism for the sodium salicylate/Glycacil® 2000 solution in Table 1 against S. aureus, P. aeruginosa, and E. coli was calculated by the method described in C. E. Kull et al., "Mixtures of Quaternary Ammonium Compounds and Long-chain Fatty Acids as Antifungal Agents", *Applied Microbiology*, 9:538–541(1961). The synergism value ($Q_A/Q_a+Q_B/Q_b$) was determined. $Q_A$ is the concentration of sodium salicylate (in percent by weight) in the mixture, which yielded 100% retardation of the bacteria, i.e., resulted in a plate count of <10 cfu/g after 14 days. $Q_a$ is the concentration of sodium salicylate alone (in percent by weight) required to yield 100% retardation of the bacteria. $Q_B$ is the concentration of Glycacil® 2000 (in percent by weight) in the mixture, which yielded 100% retardation of the bacteria. $Q_b$ is the concentration of Glycacil® 2000 alone (in percent by weight) required to yield 100% retardation of the bacteria.

When the value of ($Q_A/Q_a+Q_B/Q_b$) is less than one, the mixture is synergistic. Values for ($Q_A/Q_a+Q_B/Q_b$) of 1 and greater than 1, represent an additive effect and an antagonistic effect, respectively.

The results are shown in Table 2 below.

TABLE 2

| Preservative Mixture | $Q_A$ | $Q_B$ | $Q_a$ | $Q_b$ | $Q_A/Q_a + Q_B/Q_b$ |
|---|---|---|---|---|---|
| 0.5% Sodium Salicylate and 0.5% Glycacil ® 2000 | 0.5% | 0.5% | >1.00% | >1.00% | <1 |

The synergism for the sodium dehydroacetate monohydrate/sodium salicylate/Glycacil® 2000 solutions in Table 1 was also calculated by this method. $Q_A$, $Q_B$, $Q_a$, and $Q_b$ are defined as above. $Q_C$ is the concentration of sodium dehydroacetate monohydrate (in percent by weight) in the mixture, which yielded 100% retardation of the bacteria. $Q_c$ is the concentration of sodium dehydroacetate monohydrate alone (in percent by weight) required to yield 100% retardation of the bacteria. When the value of ($Q_A/Q_a+Q_B/Q_b+Q_C/Q_c$) is less than one, the mixture is synergistic. Values for ($Q_A/Q_a+Q_B/Q_b+Q_C/Q_c$) of 1 and greater than 1, represent an additive effect and an antagonistic effect, respectively.

The results are shown in Table 3.

TABLE 3

| Coefficient | 0.10% Sodium Salicylate, 0.50% Glycacil ® 2000, and 0.10% Sodium Dehydroacetate Monohydrate | 0.25% Sodium Salicylate, 0.25% Glycacil ® 2000, and 0.25% Sodium Dehydroacetate Monohydrate |
|---|---|---|
| $Q_A$ | 0.10% | 0.25% |
| $Q_B$ | 0.50% | 0.25% |
| $Q_C$ | 0.10% | 0.25% |
| $Q_a$ | >1.00% | >1.00% |
| $Q_b$ | >1.00% | >1.00% |
| $Q_c$ | >0.50% | >0.50% |
| $Q_A/Q_a + Q_B/Q_b + Q_C/Q_c$ | <0.8 | <1 |

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:
1. A composition comprising
   (a) iodopropynyl butylcarbamate; and

(b) (i) dehydroacetic acid or a salt thereof, (ii) salicylic acid or a salt thereof, or (iii) mixture thereof.

2. The composition of claim 1, wherin the iodopropynyl butylcarbamate is encapsulated in cyclodextrin.

3. The composition of claim 1, wherein the dehydroacetic acid or salt thereof is encapsulated in cyclodextrin.

4. The composition of claim 1, further comprising a solvent.

5. The composition of claim 4, wherein the solvent is water, an alcohol, a glycol, an ester, an ether, a polyether or any combination of any of the foregoing.

6. The composition of claim 4, wherein the solvent comprises water and alcohol.

7. The composition of claim 4, wherein the alcohol is phenoxyethanol.

8. The composition of claim 1, wherein the composition comprises a biocidally effective amount of the iodopropynyl butylcarbamate.

9. The composition of claim 1, wherein the composition comprises a fungicidally effective amount of the iodopropynyl butylcarbamate.

10. The composition of claim 1, wherein the weight ratio of the dehydroacetic acid or salt thereof to the iodopropynyl butylcarbamate ranges from about 0.0006:1 to about 1990:1.

11. The composition of claim 10, wherein the weight ratio of the dehydroacetic acid or salt thereof to the iodopropynyl butylcarbamate ranges from about 0.0063:1 to about 1400:1.

12. The composition of claim 1, wherein said composition is a use dilution comprising from about 0.00005 to about 0.4975% by weight of the dehydroacetic acid or salt thereof and from about 0.00005 to about 0.40% by weight of the iodopropynyl butylcarbamate, based upon 100% weight of total composition.

13. The composition of claim 12, wherein said composition is a use dilution comprising from about 0.0005 to about 0.35% by weight of the dehydroacetic acid or salt thereof and from about 0.0005 to about 0.15% by weight of the iodopropynyl butylcarbamate, based upon 100% weight of total composition.

14. The composition of claim 1, wherein the weight ratio of the salicylic acid or a salt thereof to the iodopropynyl butylcarbamate ranges from about 0.0006:1 to about 1990:1.

15. The composition of claim 14, wherein the weight ratio of the salicylic acid or a salt thereof to the iodopropynyl butylcarbamate ranges from about 0.0063:1 to about 1400:1.

16. The composition of claim 1, wherein said composition is a use dilution comprising from about 0.00005 to about 0.4975% by weight of the salicylic acid or a salt thereof and from about 0.00005 to about 0.40% by weight of the iodopropynyl butylcarbamate, based upon 100% weight of total composition.

17. The composition of claim 16, wherein said composition is a use dilution comprising from about 0.0005 to about 0.35% by weight of the salicylic acid or a salt thereof and from about 0.0005 to about 0.15% by weight of the iodopropynyl butylcarbamate, based upon 100% weight of total composition.

18. An antimicrobial composition comprising a synergistic mixture of:
(a) dehydroacetic acid or a salt thereof; and
(b) 3-iodo-2-propynyl butyl carbamate.

19. An antimicrobial composition comprising a synergistic mixture of:
(a) salicylic acid or a salt thereof; and
(b) 3-iodo-2-propynyl butyl carbamate.

20. An antimicrobial composition comprising a synergistic mixture of:
(a) dehydroacetic acid or a salt thereof;
(b) salicylic acid or a salt thereof; and
(c) 3-iodo-2-propynyl butyl carbamate.

21. A method of inhibiting the growth of microorganisms comprising applying an effective amount of the composition of claim 1.

22. A method of inhibiting the growth of microorganisms comprising applying an effective amount of the composition of claim 18.

23. A method of inhibiting the growth of microorganisms comprising applying an effective amount of the composition of claim 19.

24. A method of inhibiting the growth of microorganisms comprising applying an effective amount of the composition of claim 20.

25. A personal care product comprising an effective amount of the composition of claim 1.

26. The personal care of claim 25, wherein the personal care product is a shampoo, conditioner, cream, lotion, cosmetic or soap.

27. The composition of claim 1, further comprising a preservative.

28. The composition of claim 27, wherein the preservative is a quaternary ammonium chloride, a hydantoin, an isothiazolone, a paraben, chloroxylenol, chlorohexidine, phenoxyethanol, benzyl alcohol, phenethyl alcohol, benzoic acid or salts thereof, chlorobutanol, sorbic acid, tricosan, triclocarban, and any combination of the foregoing.

29. The composition of claim 28, wherein the preservative is benzethonium chloride, benzealknonium chloride, or a mixture thereof.

* * * * *